(12) United States Patent
Vammen et al.

(10) Patent No.: US 6,328,695 B1
(45) Date of Patent: Dec. 11, 2001

(54) METHOD AND AN APPARATUS FOR INVESTIGATING MATERIAL PROPERTIES OF BONE USING ULTRASOUND

(76) Inventors: Klaus Vammen, Jaegervang 29, Birkerød (DK), 3460; Kåre Christiansen, Violvej 16, Gentofte (DK), 2820; John Finnich Petersen, Stumpedyssevej 20, Hørsholm (DK), 2970

( * ) Notice: Subject to any disclaimer, the term of this patent is extended or adjusted under 35 U.S.C. 154(b) by 0 days.

(21) Appl. No.: 09/602,375

(22) Filed: Jun. 23, 2000

Related U.S. Application Data

(63) Continuation-in-part of application No. PCT/DK98/00574, filed on Dec. 22, 1998, now abandoned.

(30) Foreign Application Priority Data

Dec. 22, 1997 (DK) .................................................. 1510/97

(51) Int. Cl.[7] .............................................. A61B 8/00
(52) U.S. Cl. ...................................................... 600/442
(58) Field of Search .................................. 600/437, 438, 600/442, 449; 73/597, 599

(56) References Cited

U.S. PATENT DOCUMENTS

| | | | |
|---|---|---|---|
| 4,774,959 | * | 10/1988 | Palmer et al. ........................ 600/442 |
| 4,941,474 | * | 7/1990 | Pratt, Jr. .............................. 600/442 |
| 5,042,489 | * | 8/1991 | Wiener et al. ....................... 600/442 |
| 5,452,722 | * | 9/1995 | Langton ............................... 600/449 |
| 5,720,290 | * | 2/1998 | Buhler et al. ........................ 600/449 |
| 5,807,250 | * | 9/1998 | Ohtomo et al. ..................... 600/442 |
| 5,902,240 | * | 5/1999 | Ishii et al. ............................ 600/438 |

* cited by examiner

*Primary Examiner*—Francis J. Jaworski
(74) *Attorney, Agent, or Firm*—Thomas R. Vigil

(57) ABSTRACT

A method for investigating the mechanical properties of bone inside a live animal or human being, said method comprises launching an ultrasound pulse wave into the body of the being and establishing a trace related to the magnitude of a reflected ultrasound wave versus the time lapsed since the launching of the pulse wave. On the trace an interval in which the magnitude of the reflected ultrasound wave exhibits a steady decline versus time, is identified, and the attenuation of the ultrasound wave based on the readings of the trace within this interval is computed. The invention also provides an apparatus for adapted for providing diagnostic information concerning the mechanical properties of bone.

22 Claims, 3 Drawing Sheets

METHOD AND AN APPARATUS FOR INVESTIGATING MATERIAL PROPERTIES OF BONE USING ULTRASOUND

CROSS-REFERENCE TO RELATED APPLICATIONS

This is a continuation-in-part of International Patent Application PCT/DK98/00574 with an international filing date of Dec. 22, 1998, now abandoned. This application is based on application No. 1510/97 filed in Denmark on Dec. 22, 1997, the contents of which are incorporated hereinto by reference.

BACKGROUND OF THE INVENTION

1. Field of the Invention

The present invention relates to a method and to an apparatus for investigating the mechanical properties of tissue inside a live animal or human being. In particular, the present invention relates to the use of ultrasound for assessment of the mechanical properties of tissue. The invention more particularly relates to methods of investigating the mechanical properties of a material which may not be easily accessible and which may not be adequately described by simple theoretical models. The invention further relates to a method of investigating the mechanical properties of bone in vivo.

The investigation of the mechanical properties of bone in vivo is of great interest in view of the occurrence of osteoporosis. Osteoporosis may be defined as a long-term metabolic deficiency causing an unbalance in the natural process of bone resorbtion and bone rebuilding with the result of a loss of mechanical strength and increased risk of fractures. The degradation of the mechanical strength of the bones may proceed to a stage where even minimal trauma result in bone fractures. It has been estimated that osteoporosis affects from 10–20% or maybe even more of the female population and about 10% of the male population above the age of 50.

Treatments do exist which may delay or reverse the progression of osteoporosis. However, effective methods permitting an accurate diagnosis to be established at an early stage and permitting accurate monitoring of patient response to medication would be of great value.

Nevertheless, the accurate assessment of osteoporosis is difficult. The bones in the skeleton are by nature non-homogeneous and different parts of the skeleton may not be affected to the same degree. The material strength of the bones naturally changes over time, reaching a maximum about the age from 20–30 years and gradually declining later on. Individual differences may be substantial. Furthermore, the mechanisms involved and the factors controlling this process may not be fully understood.

2. The Prior Art

U.S. Pat. No. reissue Re32,782 discloses a method for determining in vivo strength of bone in a live being. According to this method, a first transducer launches an acoustic pulse though a bone and surrounding soft tissue, which pulse is received by a second transducer. The distance between the transducers is measured and so is the transit time of the pulse between the transducers. These measurements form the basis for determining the effective velocity of the pulse through the bone and surrounding soft tissue, which velocity provides one piece of information used for evaluating the strength of the bone.

The measurements of the distance and of the transit time in respect of an acoustic pulse launched through the bone with surrounding soft tissue provides no positive information about the path followed by the acoustic pulse. This may disturb the conclusions as the path may be non-linear due to refraction effects and as the acoustic transducers may exhibit strong sensitivity variations on varying orientations, both of which factors introduce potential sources of errors in case of accidental misalignments between the transducers. As the pulse is likely to have traveled through sections of soft tissue and through sections of bone tissue, any effect due to variations in bone structure may be buried in variations caused by other factors.

U.S. Pat. No. 5,038,787 discloses a method for analyzing material properties using reflected ultrasound. According to this method, a bone is placed in a separating medium that includes water and soft tissue and then subjected to ultrasound pulse waves from varying angles of incidence while the respective reflected waves are received and analyzed. The varying angles of incidence are obtained by shifting the transmitting transducer around. Critical angles of reflection are established and used in the calculation of a matrix of mechanical parameters such as elasticity.

The prior art also comprises a suggestion for providing a pair of transducers coaxially in a water tank, submerging a bone sample between the transducers, launching ultrasound pulses in various frequencies ranging from 0.2 MHz to 0.8 MHz and measuring the attenuation as a function of frequency.

In this method, any loss of signal will for the sake of the calculation be presumed as due to attenuation. This may amount to a misinterpretation, e.g. in case the loss was due to reflection, likely to arise whenever the pulse wave crosses some interface, e.g. water to soft tissue. In addition, this method does not separate contributions caused by effects in the soft tissue from contributions caused by effects in the bone tissue.

U.S. Pat. No. 4,408,492 refers in the context of ultrasonic echoscopy to the principle of time gain compensation, understood as the concept of increasing the gain of the receiver in proportion to the echo time delay in order to compensate for the progressive attenuation sustained by echoes from reflecting surfaces deeper within the object. The publication mentions the definition of a first and a second contour within the object subjected to the examination, the determination of the attenuation exhibited between the first and second contours and the use of the time gain compensation facility as necessary to compensate for the attenuation as determined. The purpose of this method is to overcome the problem of shadowing in a situation where a local highly absorbent area obscures deeper lying information.

U.S. Pat. No. 4,414,850 pertains to a measurement method and a system for measuring characteristics of attenuation of domains in an object, by which method ultrasonic waves are transmitted into the object and reflected ultrasonic waves are received and analyzed. Attenuation of the reflected waves is presumed to be a linear function of frequency. Attenuation coefficients are determined for various domains within the body.

U.S. Pat. No. 4,941,474 relates to a multi-variable analysis of bones for the purpose of detecting abnormal bone conditions. One method explained comprises launching into the patient an ultrasonic signal having components in the spectrum from about 100 kHz to about 600 kHz, receiving reflected signals, and evaluating the magnitude on the received signals.

SUMMARY OF THE INVENTION

The invention, in a first aspect, provides a method for investigating the mechanical properties of bone inside a live animal or human being, comprising
- launching an ultrasound pulse wave into the body of the being and into the bone,
- monitoring the ultrasound wave reflected from the body and establishing a trace related to the magnitude of the reflected ultrasound wave versus the time lapsed since the launching of the pulse wave,
- identifying a pair of points on the time scale delimiting an interval in which the logarithm of the magnitude of the reflected ultrasound wave exhibits a steady decay versus time, and which interval corresponds with a section of bone estimated to predominantly comprise trabecular bone,
- selecting at least two points on the time scale within the interval defined by the pair of points and reading from the trace corresponding values of reflected wave magnitude,
- reading the time delay between the selected points,
- computing the distance between those points in the bone which correspond with the selected points, using the sound velocity estimated in respect of wave propagation through trabecular bone, and
- computing the attenuation of the ultrasound wave based on the readings corresponding with the selected points.

This method produces information useful for characterizing bone inside a live animal or human being which information may provide a valuable part of the background for diagnosing e.g. osteoporosis. The method according to the invention permits retrieval of information related to trabecular bone, singling out these data from signals related to other kinds of tissue. The method according to the invention makes it feasible to use a high range of frequencies, by which it is possible to focus investigation on minute zones of interest.

Trabecular bone, sometimes also referred to as cancellous bone, forms only part of the bone structure. Trabecular bone may be explained as a porous structure comprising a network of mineralized collagen fibrils and marrow (fat). A piece of trabecular bone is generally sheathed within or enclosed by a layer of cortical bone, which comprises a more dense structure. In long bones, the central part of the bone has a tubular shape mainly comprised of a wall of cortical bone. Towards the ends of the long bones, the cortical walls become thinner and increase in diameter as they form the bone end portions, where most of the volume enclosed by the cortical walls is filled with trabecular bone consisting of plates, spicules or small septums of cancellous bone.

The pattern of age related bone loss differs between cancellous and cortical bone. Commonly, trabecular bone decreases in number of septums rather than thickness. Cortical bone usually becomes more porous and the cortical walls also become thinner. These changes in structure give rise to corresponding changes in acoustical properties, the increasing porosity of cancellous bone giving rise to a decrease in acoustic attenuation. Some data of acoustic properties of different kinds of tissue are listed in the table below.

Table of physical properties of tissue

|  | Density g/cm$^3$ | Speed of Sound mm/$\mu$s | Attenuation dB/cm |
|---|---|---|---|
| Cortical tissue | 2.00 | 3.50 | 6.90 |
| Trabecular tissue | 1.06 | 1.89 | 1.9 to 15.7 |
| Fat | 0.93 | 1.48 | 1.00 |

In the progress of osteoporosis, structural bone tissue is replaced with fat, which exhibits a lower value of acoustical damping.

Although the changes take place in cortical bone as well as in trabecular bone, trabecular bone due to its occurrence in more bulky regions of a homogeneous structure seems to offer the prospect of a more accurate characterization by acoustic methods and thus the chance of detecting any change at an early stage. Acoustic characterization of trabecular bone has, however, been difficult in methods according to the prior art since the cortical bone reflects most of the acoustic energy, making it difficult to retrieve any useful data from the layer below. However, these problems are overcome by the method according to the invention.

According to this method, a trace of the logarithm of the magnitude of an ultrasound pulse, plotted versus time of flight is relied on for retrieving information about a bone tissue inside a live animal or human being. The method is non-invasive and does not require direct access to the tissue under investigation. Providing a plot of the logarithm of the amplitude permits overviewing a wide dynamic range within a single frame of display and permits direct reading of attenuation factors.

As known in the art, the traces are likely to exhibit sections of steady decay but possibly also peaks or sanctions of level offsets. Such sections of peaks or level offsets are likely to arise in cases where the ultrasound pulse traverses an interface between regions of different acoustic impedance. Sections of steady decay are likely o be related to regions of tissue, which are homogeneous on a macroscopic level, although likely to be non-homogeneous on a microscopic level. The microscopic inhomogenities will give rise to scattering and reflection of the ultrasound pulse. The transmitted pulse as well as any reflections is subjected to attenuation on passing through the tissue.

In sections of steady decay of the trace, the corresponding regions of tissue may be presumed to comprise distributed but mutually similar, microscopic non-homogeneities in order that the ratio of reflected energy to transmitted energy is the same in any sub-region thereof.

Based on this presumption, the attenuation in the corresponding region of tissue may be computed by comparing readings along the trace, which in effect amounts to comparing levels of reflections from different minute non-homogeneities to each other and relating them to the distance from the transducer.

In an object comprising a boundary or a transition with a rather steep change of acoustic impedance, this transition will give rise to reflection of a substantial proportion of the acoustic energy.

As an acoustic transducer according to the state of the art generally provides a reflecting surface on its own, any pulse reflected into the transducer may be reflected from the transducer to re-enter the test object where it may be subjected to a renewed reflection. The result is that one boundary in the object may manifest itself by a trace which includes several spikes, effectively repeating or mirroring the image of the first spike and confusing the display. The step of identifying an interval of the trace exhibiting a steady decline is important with the view of avoiding falsifications of the data due to such mirroring.

According to a preferred embodiment, the trace of the reflected wave magnitude is established by detecting peak levels of a high frequency signal received from the transducer. Evaluation of the peak-detected signals permits a simplification of the data processing.

According to preferred embodiments, the launching of the ultrasound pulse wave is carried out by placing an ultrasound transducer in contact with the skin. The transducer coupling to the skin may be enhanced by applying a layer of gel to the skin prior to the application of the transducer. This provides a simple procedure, which combines accuracy in the measurement with convenience to the person who is the subject for the analysis.

According to a preferred embodiment, the same ultrasound transducer is used for launching the ultrasound pulse wave and for monitoring the reflected ultrasound wave. The use of a single transducer rather than a combination of a transmitter transducer and a receiver transducer simplifies the handling and avoids potential errors related to misalignment or mismatching.

According to a preferred embodiment, the ultrasound pulse wave is launched by a transducer that is adapted for delaying the transmitted pulse wave as well as the received pulse wave. The delay feature spaces the advent of multiple reflections on the time scale from the advent of the initial reflection, usually preferred for purposes of interpreting the results. The delay feature is important in applications where the task object comprises a transition zone of strong reflection in the upper layer close to the transducer surface and where the information wanted relates to structures beyond such transition zone. The delay should preferably by adapted to space any mirror images of pronounced spikes away from the region to be analyzed. This simplifies data interpretation and enhances accuracy in the measurements.

According to a further preferred embodiment, the transducer may be adapted to produce focused waves in order that the zone of investigation is narrowed down for enhanced resolution. A focused transducer is adapted to emit a focused beam of ultrasonic waves. Due to the reciprocal nature of the transducer, the sensitivity may be concentrated in a similar area.

Focusing the transducer narrows down the zone of sensitivity and suppresses sensitivity to signals from other directions. Focusing an ultrasonic transducer may e.g. be achieved by adapting the transducer front surface to be curved concavely towards the focal point or by designing the active surface of the transducer in a pattern of planar, annular, concentric rings, which are controlled electrically so as to be fired sequentially in order to provide a focusing effect.

Due to well-known geometric aspects, the width of the active area covered by the beam is linked to the spacing from the transducer, i.e. the effectiveness in the focusing is dependent on the distance. The focused transducer may to advantage be combined with a delay line, provided the focal length is adapted to compensate for the delay line. The delay line spaces the transducer from the test object and makes it possible to achieve a proper focusing by means of a transducer which is adapted to operate in more like a far field condition rather than in a near field condition. A focused transducer used in a far field situation provides the advantage of the effective beam width being uniform over a greater range of distances.

According to a preferred embodiment, the ultrasound wave used comprises a pulse enveloping a signal oscillating at a frequency in the range between 0.5 and 5.0 MHz. The lower boundary of this interval is restricted in view of considerations related to resolution and of the lack of focusing possible at the greater wavelengths at lower frequencies. The upper boundary in this interval is restricted in view of considerations concerning attenuation in relation to the required range.

The invention, in a second aspect, provides a method for investigating the mechanical properties of bone inside a live animal or human being, comprising launching an ultrasound pulse wave at a first frequency and at a second frequency into the body of the being and into the bone, monitoring the ultrasound waves reflected from the body and establishing respective traces related to the magnitude of the reflected ultrasound waves versus the time lapsed since the launching of the pulse waves, identifying in respect of each trace a pair of points on the time scale delimiting an interval in which the logarithm of the magnitude of the reflected ultrasound wave exhibits a steady decay versus time, and which interval corresponds with a section of bone estimated to predominantly comprise trabecular bone, selecting at least two points on the time scale within the interval defined by the pair of points related to a first one of said traces and reading from both traces corresponding values of reflected wave magnitude, reading the time delay between the selected points, computing the distance between those points in the bone which correspond with the selected points, using the sound velocity estimated in respect of wave propagation through trabecular bone, and computing in respect of each trace the attenuation of the ultrasound wave based on the readings corresponding with the selected points, and combining the respective computed values to establish an expression relating the attenuation to frequency.

By this method, the relation between attenuation and frequency is established in respect of the investigated structure. This together with the data of attenuation at the respective frequencies provides a comprehensive characterization of the tissue under investigation, widening the base of data available for drawing any conclusions.

According to a preferred embodiment the attenuation vs. frequency is presumed to be proportionate to a function of the type $f^b$, i.e. f lifted to the power of b, where the base f represents the frequency, the exponent b is a constant related to a physical property of the test object, and wherein values obtained by measurements at a first frequency and at a second frequency are used to calculate the exponent b.

The applicants have discovered that the expression $f^b$ seems to provide a more useful mathematical approximation of the attenuation vs. frequency than a presumption generally prevailing in the prior art, namely that attenuation is simply proportionate to frequency. The applicants have discovered that the exponent b seems to provide a most useful piece of information for estimating the bone status such as a state of osteoporosis. The invention provides a method of obtaining a reliable estimate of the exponent b and thereby offers the prospect of an early indication of a situation of importance.

The invention, in a third aspect, provides an apparatus adapted for providing a piece of diagnostic information concerning the mechanical properties of bone inside a live animal or human being, said apparatus comprising means for launching an ultrasound pulse wave into the body of the being and into the bone, means for monitoring the ultrasound wave reflected from the body and for establishing a trace related to the magnitude of the reflected ultrasound wave versus the time lapsed since the launching of the pulse wave, in order to enable an operator to identify a pair of points on the time scale delimiting an interval in which the logarithm of the magnitude of the reflected ultrasound wave exhibits a steady decay versus time, and which interval corresponds with a section of bone estimated to predominantly comprise trabecular bone, to select at last two points on the time scale within the interval defined by the pair of points and to read from the trace corresponding values of reflected wave magnitude, to read the time delay between the selected points, to compute the distance between those points in the bone which correspond with the selected points, using the sound velocity estimated in respect of wave propagation through trabecular bone, and to compute the attenuation on the ultrasound wave based on the readings corresponding with the selected points.

Further features and advantages of the invention will appear from the following detailed description of preferred embodiments, which is given with reference to the drawings.

BEST MODE FOR CARRYING OUT THE INVENTION

All figures are schematic and not to scale and illustrate only the details necessary for enabling those skilled in the art to practice the invention while other details have been omitted for the sake of clarity. In all figures, the same references are used to designate identical or corresponding items.

Figure 1:
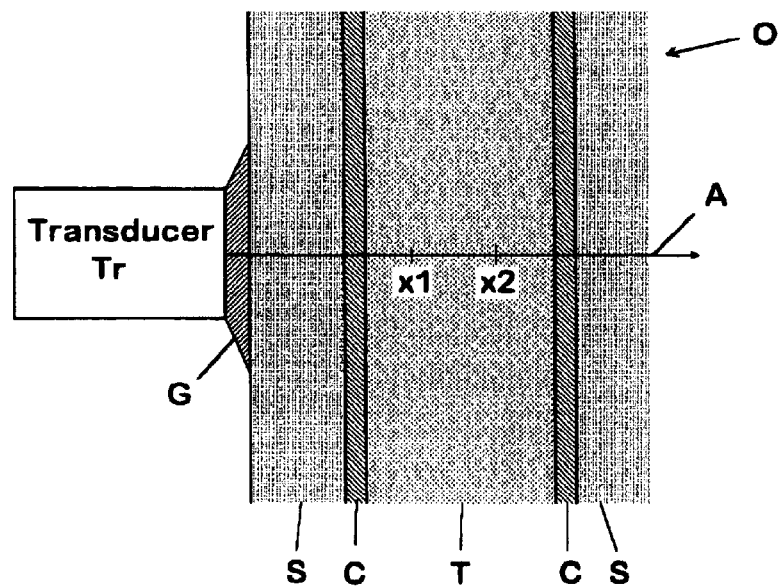
FIG. 1 is a cross section through an object contacted by an acoustic transducer, the section including the axis of the transducer.

FIG. 1 illustrates in section a transducer Tr coupled by means of an intermediate layer of ultrasonic gel G to an object, e.g. a human extremity (calcaneum, patella, ulna, phalanx or other). For the purposes of this explanation, it is sufficient to say that the object O, explained as occurring in the direction from the transducer, comprises a layer of skin tissue S, a layer of cortical bone C, a layer of trabecular bone T, another layer of cortical bone C and another layer of skin tissue S.

The transducer emits an acoustic pulse beam generally focused to propagate with a maximum of intensity along the axis A. Generally speaking, the acoustic pulse beam will be smeared out transversely in some region centered along the axis A. It lies within the capabilities of those skilled in the art to estimate the width of the beam at respective depths of penetration.

According to a preferred embodiment, the transducer includes a delay line feature.

FIG. 1 indicates two locations, $x_1$ and $x_2$, spaced apart and located on the beam axis A. These points will be referred to later in the explanation.

Figure 2:
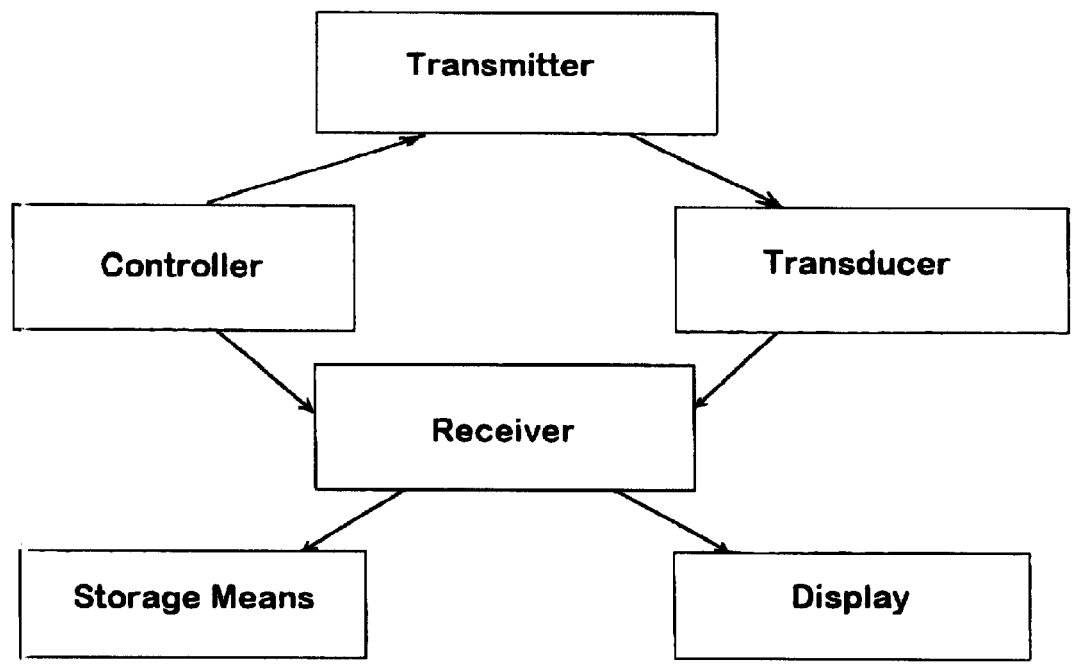
FIG. 2 is a block diagram illustrating basic components of the instrumentation used.

FIG. 2 illustrates a block diagram of the instrumentation used in a preferred embodiment. The instrumentation basically comprises a transducer, a transmitter, a receiver, a storage means, a display and a controller.

The transducer serves the purpose of transmission as well as the purpose of reception of the acoustical wave. In the preferred embodiment, the transducer is specified as being resonant at 2 MHz, with a bandwidth of 30 to 40% and provided with a damping feature serving the purpose of enhancing impulse response.

The transducer is connected to a transmitter, which provides the drive signal for causing the transducer to launch an ultrasonic pulse. The transmitter is adapted for outputting short pulse bursts, each pulse enveloping e.g. a few cycles of oscillation of the transducer. The transmitter is triggered by a signal emitted from the controller.

The transducer is also connected to a receiver, which processes the signal received by the transducer in order to provide on its output a rectified peak signal, which may be averaged over time in order to suppress random error signals. The receiver also receives a synchronization signal from the controller, enabling it to suppress the powerful signal caused by the transmitter drive pulse.

A display is connected to receive the receiver output signal and adapted to present a trace of peak-detected amplitude versus time. The output signal is also fed to a storage means where the signal is recorded for later processing.

Figure 3:
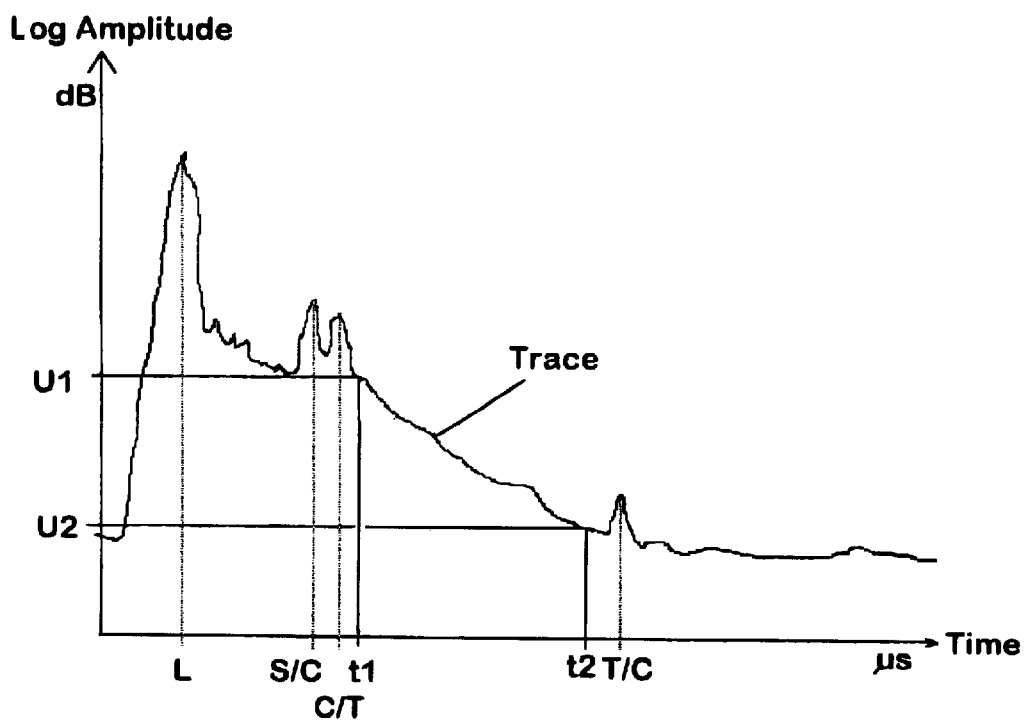
FIG. 3 is a trace produced on the display of the instrumentation, using a single frequency of excitation.

Reference is now made to FIG. 3 for a depiction of the trace on the display and for an explanation of the processing of the data. In FIG. 3, the x-axis is calibrated in microseconds. Although actually representing time, the x-axis is for many purposes interpreted as a scale of distance from the transducer. In view of the different acoustic velocities of the tissues involved, this may not be strictly true, however, it may for many purposes represent an acceptable approximation.

The y-axis used for the amplitude is calibrated in decibels, signifying that it represents the logarithm of the relative amplitude.

The trace in FIG. 3 shows an initial steep rise and then a more gradual decay superimposed with a number of localized peaks or deflections. The first peak L is regarded to signify the spill-over effect from the launching of the pulse wave, a second peak S/C is attributed to a reflection at the skin/cortical bone interface, a third peak C/T is attributed to a reflection at the cortical bone/trabecular bone interface and a fourth peak T/C is attributed to be caused by the trabecular bone/cortical bone interface. After the fourth peak the trace settles around a fairly constant level, which is presumed to signify a background of noise. Between the third and the fourth peak, it is possible to identify an interval of steady decline in the trace.

The operator in charge of carrying out the measurement will evaluate the trace and will refer to his knowledge concerning the anatomy of the site investigated in order to correlate various aspects of the trace with the topology and various properties concerning the site investigated.

Thus the person in charge of the analysis will use his skill to verify that the interval of steady decline indeed relates to a section of trabecular bone, and that the trace within this interval represents valid data, not based by a background of noise and not affected by reflections related to other causes. Two points $t_1$ and $t_2$ within this interval are selected. From the trace, corresponding amplitude values $U_1$ and $U_2$ are read.

The pulse peak amplitude as a function of distance within a homogeneous region is presumed to obey the equation $$U(x)=U(x_0)+\exp(-\alpha^*x)$$

where U is the amplitude, X is the distance and $\alpha$ is the spatial attenuation factor. Writing into this formula measurement data from the readings at two points $x_1$ and $x$ corresponding to the time instance of $t_1$ and $t_2$, it may be shown that:

$$\alpha = \frac{\ln U(x_1) - \ln U(x_2)}{x_1 - x_2}$$

The distance $x_1-x_2$ may be computed from the time delay multiplied wish the speed of sound of the respective tissue.

Thus from the example in the FIG. 3 where $t_1=32$ μs, $t_2=59$ μs, $U_1=32$ dB and $U_2=4$ dB, we have $$\alpha=-(32-4)dB/(32\ \mu s-59\ \mu s)=1.037\ dB/\mu s.$$

Assuming a speed of sound of 0.189 cm/μs, this converts into $$\alpha=(1.037\ dB/\mu s)/(0.189\ dB/\mu s)=5.49\ dB/cm$$

Figure 4:
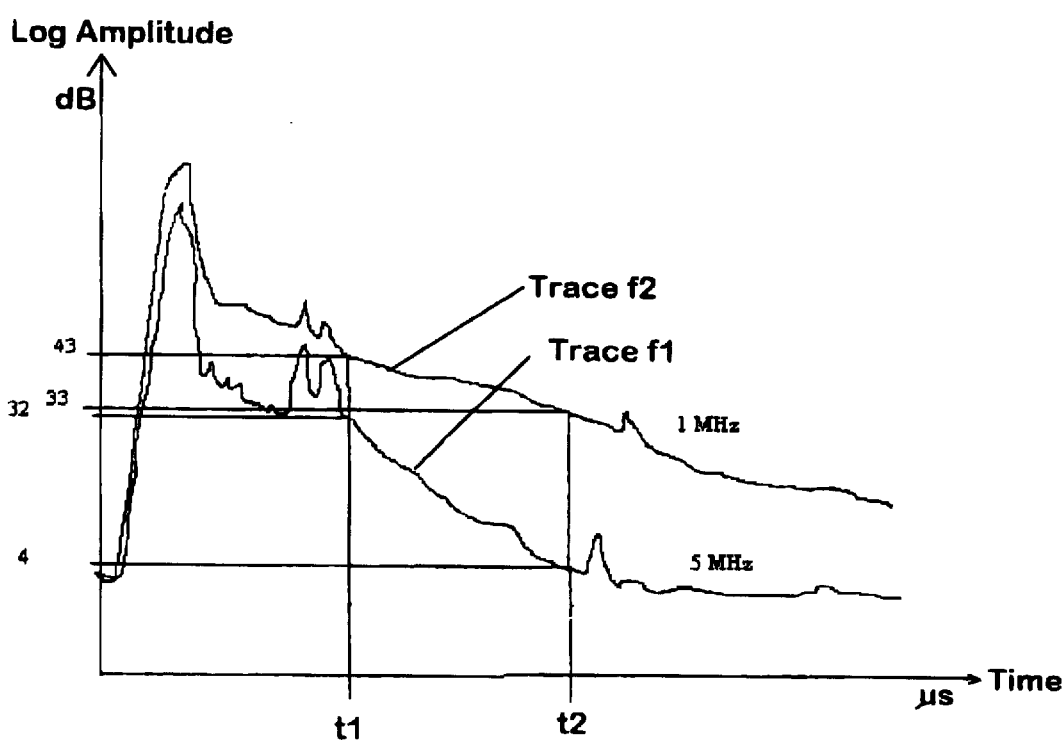
FIG. 4 is a double trace produced on the display of the instrumentation in respect of two different frequencies of excitation.

Reference is now made to FIG. 4 for the explanation of a procedure involving measurements taken at two different frequencies. FIG. 4 illustrates a trace f1 identical to tie trace of FIG. 1 and recorded using a transducer pulse frequency of 5 MHz. In addition, FIG. 4 includes a second trace f2 recorded under identical circumstances except that the recording has been taken using a transducer pulse frequency of 1 MHz.

The trace produced at 1 MHz exhibits a shape basically similar to that of the first trace but with a more flat slope attributed to the lower attenuation of the tissue as measured at the lower frequency.

The frequency dependency of the attenuation may be accounted for in the above formula by taking $\alpha$ to be instead of a constant value, a function of the frequency as $$\alpha(f)=a^*f^b$$

where a and b are two parameters specific to the object whereas f is the frequency.

Once two values of alpha, i.e. $\alpha_1$ and $\alpha_2$, have been established in respect of two different frequencies, $f_1$ ad $f_2$, the physical parameters a and b may be computed according to the following:

$$\alpha_1=a^*f_1^b$$

$$\alpha_2=a^*f_2^b$$

from which $$b=\ln(\alpha_1/\alpha_1)/\ln(f_1/f_2)$$

$$a=\alpha_1/f_1^b$$

The second last of these equations is equivalent to $$b=\log(\alpha_1/\alpha_2)/\log(f_1/f_2)$$

In respect of FIG. 4 and using for the first frequency ($f_1=5$ MHz) data referred to in relation to FIG. 3, we may complement these data with the amplitude readings 43 dB and 33 dB in respect of the second frequency ($f_2=1$ MHz) from which we have $$\alpha_1=5.49\ dB/cm$$

$$\alpha_2=-(43-33)dB/(32-59)\mu g=0.370\ dB/)\mu s$$

$$\alpha_2=0.370\ dB/0.189\ cm=1.95\ dB/cm$$

$$b=\log(5.49/1.95)/\log(5/1)$$

$$b=0.4495/0.694=0.643$$

$$a=5.49/5^{0.643}=1.95\ dB\ cm^{-1}\ MHz^{-b}$$

Thus the value of the exponent b has been calculated to 0.643.

Inserting these values into the expression for $\alpha$ as a function of the frequency, we have $$\alpha(f)=1.95^*f^{0.643}\ dB\ cm^{-1}\ MHz^{-0.643}$$

Figure 5:
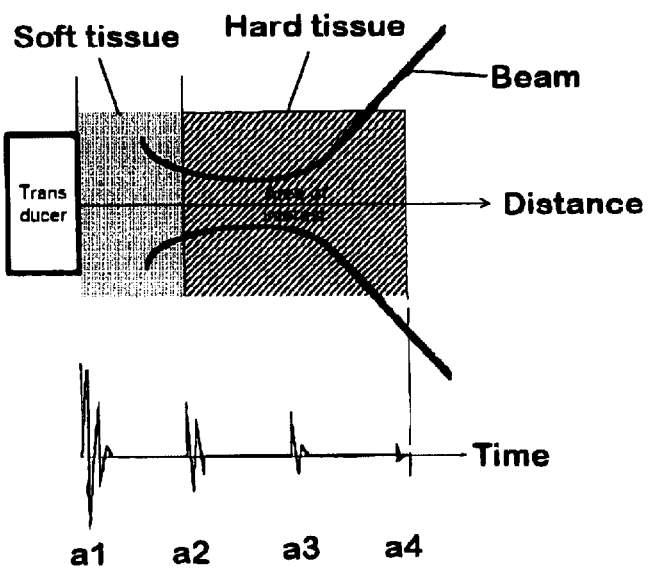
FIG. 5 is a symbolic figure illustrating in its upper part a cross section through an object contacted by a strongly focused acoustic transducer, the section including the axis of the transducer, while the figure in its lower part illustrates a time plot of the reflected signal received by the same transducer.
Figure 6:
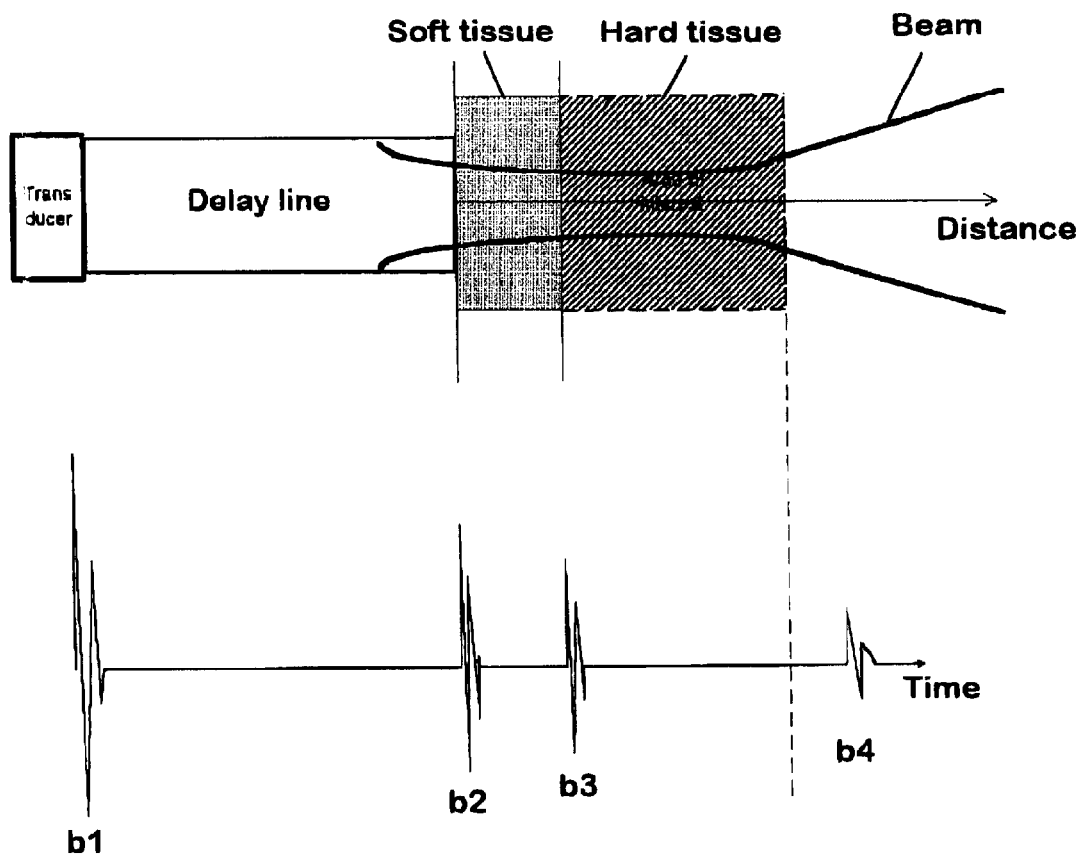
FIG. 6 illustrates a figure similar to FIG. 5 but of an embodiment modified to include a delay line in contact with a mildly focused transducer.

Reference is now made to FIGS. 5 and 6 for an explanation regarding aspects of combining a transducer with a delay line, FIG. 5 depicting a situation with a sharply focused transducer in contact with a test object, and FIG. 6 depicting a situation with a mildly focused transducer and with a delay line interposed between the transducer and the test object.

FIG. 5 is effectively in two parts. The upper part depicts a cross section through the transducer and through the object contacted by the transducer, the section taken by a plane that includes the transducer axis. The transducer is presumed to launch a pulse, which propagates through a layer of soft tissue into a layer of hard tissue, which includes the area of interest. Waves reflected from any boundaries on the way are picked up by the same transducer and plotted versus the time lapsed.

The lower part of FIG. 5 is the time plot depicting the reflected wave received by the transducer. In this plot the scaling on the time axis has been adjusted in order to make the time plot immediately comparable to the section above. Thus the time scale has been multiplied by a factor which reflects the propagation velocity and which takes into account the fact that the ultrasonic wave travels forth and back.

The time plot reveals four spikes referred to as a1, a2, a3, and a4, respectively. The spikes have peak amplitudes decaying according to their spacing from the starting paint to the left.

The first spike, a1, is easily correlated with the interface between the transducer and the soft tissue contacted by the transducer. The second spike, a2, is also easily correlated with the boundary between the soft tissue and the hard tissue. The remaining spikes, a3 and a4, seem to suggest the presence of further boundaries within the specimen, however, they more likely represent repeated reflections, i.e. spikes produced by the launched pulse traveling from the transducer to the most imminent surface of the hard tissue, and back more than once.

Reference is now made to FIG. 6 which illustrates a situation similar to the one illustrated in FIG. 5 except for the facts that a delay line has now been interposed between the transducer front surface and the surface of the soft tissue contact and that the type of transducer is different. The delay line is a body of matter capable of transmitting ultrasound without causing scattering or reflections and adapted for spacing the advent of reflections in time. A preferred delay time is 20–30 $\mu s$. According to preferred embodiments, the delay line comprises a body of water enclosed within a container, a slab of a polymer or a slab of metal or ceramics with excellent sound propagation capability. The delay to a wave train propagated through a body of water of a length of 50 mm may be computed as 50 mm/(1.89 mm/$\mu s$)=26 $\mu s$.

A preferred embodiment comprises a container holding a body of water and with a front that provides an acoustic window for interfacing with the object to be investigated by the ultrasound method. The acoustic window comprises a stratum or a disk of a matter selected for providing an acoustic impedance, which matches the acoustic impedances of the water and of the object.

In case of a human body, the acoustic impedance, i.e. sound velocity, multiplied by density, is estimated at 1.53 kg/($m^2$*s). In case of water, the acoustic impedance is 150 kg/($m^2$*s). A disk of a TBX polymer, found to have an acoustic impedance of 1.51 kg/($m^2$*s), has been found to work well. Generally a window with an acoustic impedance intermediate the values of the acoustic impedances of adjacent layers is transparent to the ultrasonic waves and thus transmits a maximum of energy while causing a minimum of reflections.

The time plot in FIG. 6 illustrates spikes b1, b2, b3, and b4. The spike b1 correlates with the interface between the transducer and the delay line front surface. The spike b2 correlates with the interface between the delay line back surface and the front surface of the soft tissue. The spike b3 correlates with the interface between soft tissue and hard tissue, and the spike b4 illustrates a mirror image similar to a3 in FIG. 5.

However, FIG. 6 clearly shows how the mirror image spike b4 has been spaced in time by an offset sufficient to avoid confusing this spike with any signals received from the area of interest. This simplifies interpretation of the plot and provides for enhanced accuracy of any readings.

The FIGS. 5 and 6 also show computed curves delimiting the zone covered by respective focused transducers in older to show the difference of properties. In either case the criterion for selecting the transducer type has been to provide a focused transducer adapted for covering an area of a predetermined beam width within the area of interest. However, due to reasons of wave propagation geometry, the beam width varies with the distance, thus the required width is only obtained within a particular range of distances.

In the case of FIG. 5, the transducer is rated as covering a beam width at 4.3 mm at distances ranging from 23 mm to 36 mm. However, in order to focus at such short distances where the transducer must operate within or adjacent to the near field, the transducer has to be adapted for a rather pronounced focusing feature. This has the consequence that the true effective beam width varies substantially within the area of interest as shown in FIG. 5, depending on the distance from the transducer.

In the case of FIG. 6, the transducer is rated for covering a beam width of 11 mm at distances ranging from 43 mm to 103 mm. Due to the longer distance this kind of beam width pattern is obtained by means of a transducer with a moderate degree of focusing. As a result, the true beam width shows less variation within the area of interest, as will appear from FIG. 6. Thus the sensitivity tends to be more uniform over the area of interest and more easily predictable.

Although specific methods have been described above in specific contexts, such methods are not excluded from use in other contexts, from combination in other ways and for being used for other purposes. The preceding description is offered with the sole purpose of illustrating the invention and is not intended to limit the scope thereof, which is exclusively defined by the appended claims.

We claim:

1. A method for investigating the mechanical properties of bone inside a live animal or human being, comprising
    launching an ultrasound pulse wave into the body of the being and into the bone,
    monitoring the ultrasound wave reflected from the body and establishing a trace related to the magnitude of the reflected ultrasound wave versus the time lapsed since the launching of the pulse wave,
    identifying a pair of points on the time scale delimiting an interval in which the logarithm of the magnitude of the reflected ultrasound wave exhibits a steady decay versus time, and which interval corresponds with a section of bone estimated to predominantly comprise trabecular bone, selecting at least two points on the time scale within the interval defined by the pair of points and reading from the trace corresponding values of reflected wave magnitude, reading the time delay between the selected points, computing the distance between those points in the bone which correspond with the selected points, using the sound velocity estimated in respect of wave propagation through trabecular bone, and computing the attenuation of the ultrasound wave based on the readings corresponding with the selected points.

2. The method according to claim 1, wherein said trace of reflected wave magnitude is established by detecting peak levels of a high-frequency signal received from the transducer.

3. The method according to claim 1, wherein the step of launching of the ultrasound pulse wave is carried out by placing an ultrasound transducer in contact with the skin and operating said transducer to transmit the ultrasound pulse wave.

4. The method according to claim 3, wherein a thin layer of gel is applied to the skin prior to the step of placing the transducer in order to enhance the coupling of acoustic energy from the transducer into the skin.

5. The method according to claim 3, wherein the monitoring of the reflected ultrasound wave is carried out by using the same ultrasound transducer for launching the ultrasound pulse wave as well as for picking up the reflected ultrasound wave.

6. The method according to claim 3, wherein the step of launching of the ultrasound pulse wave is carried out by using a transducer that is adapted for delaying the launching and the picking up of pulse waves.

7. The method according to claim 3, wherein the step of launching of the ultrasound pulse wave is carried out by using a transducer that is adapted for transmitting a focused beam of ultrasound waves.

8. The method according to claim 3, wherein said ultrasound transducer comprises an acoustic window formed buy a disk for interfacing between the object to be investigated and the remainder of said transducer, which disk comprises a material selected for providing an acoustic impedance intermediate the respective values of acoustic impedance pertaining to the object and to the remainder of said transducer.

9. The method according to claim 8, wherein attenuation versus frequency is presumed to be proportional to a function of the type f lifted to the power of b, where the base f represents the frequency and the exponent b a constant, and comprising the use of the computed values to calculate the exponent.

10. The method according to claim 1, wherein the ultrasound wave comprises a burst pulse, comprising a signal oscillating at a frequency in the range between 0.5 and 5 MHz.

11. The method according to claim 1, wherein the attenuation is computed as an average based on a number of points selected within the interval defined by said pair of points.

12. A method for investigating the mechanical properties of bone inside a live animal or human being, comprising launching an ultrasound pulse wave at a first frequency and at a second frequency into the body of the being and into the bone, monitoring the ultrasound waves reflected from the body and establishing respective traces related to the magnitude of the reflected ultrasound waves versus the time lapsed since the launching of the pulse waves, identifying in respect of each trace a pair of points of the time scale delimiting an interval in which the logarithm of the magnitude of the reflected ultrasound wave exhibits a steady decay versus time, and which interval corresponds with a section of bone estimated to predominantly comprise trabecular bone, selecting at least two points on the time scale within the interval defined by the pair of points related to a first one of said traces and reading from both traces corresponding values of reflected wave magnitude, reading the time delay between the selected points, computing the distance between those points in the bone which correspond with the selected points, using the sound velocity estimated in respect of wave propagation through trabecular bone, and computing in respect of each trace the attenuation of the ultrasound wave based on the readings corresponding with the selected points, and combining the respective computed values to establish an expression relating the attenuation to frequency.

13. An apparatus adapted for providing a piece of diagnostic information concerning the mechanical properties of bone inside a live animal or human being, comprising means for launching an ultrasound pulse wave into the body of the being and into the bone, means for monitoring the ultrasound wave reflected from the body and for establishing a trace related to the magnitude of the reflected ultrasound wave versus the time lapsed since the launching of the pulse wave, in order to enable an operator to identify a pair of points on the time scale delimiting an interval in which the logarithm of the magnitude of the reflected ultrasound wave exhibits a steady decay versus time, and which interval corresponds with a section of bone estimated to predominantly comprise trabecular bone, to select at least two points on the time scale within the interval defined by the pair of points and to read from the trace corresponding values of reflected wave magnitude, to read the time delay between the selected points, to compute the distance between those points in the bone which correspond with the selected points, using the sound velocity estimated in respect of wave propagation through trabecular bone, and to compute the attenuation of the ultrasound wave based on the readings corresponding with the selected points.

14. The apparatus according to claim 13, comprising an ultrasound transducer suited for placement in contact with the skin and adapted for transmitting an ultrasound pulse wave.

15. The apparatus according to claim 14, wherein said ultrasound transducer is adapted for picking up a reflected ultrasound wave.

16. The apparatus according to claim 14, wherein said ultrasound transducer is provided with delay means for delaying the transmission and the picking up of pulse waves.

17. The apparatus according to claim 16, wherein said delay means is adapted for delaying the transmission by a time delay in the range from 20 µs to 30 µs.

18. The apparatus according to claim 16, wherein said delay means comprises a container enclosing a body of water.

19. The apparatus according to claim 14, wherein said ultrasound transducer is adapted for transmitting a focused beam of ultrasound waves.

20. The apparatus according to claim 14, wherein said ultrasound transducer is adapted for transmitting a burst pulse, comprising a signal oscillating at a frequency in the range between 0.5 and 5 MHz.

21. The apparatus according to claim 14, wherein said ultrasound transducer comprises an acoustic window formed by a disk for interfacing between the object to be investigated and the remainder of said transducer, which disk comprises a material selected for providing an acoustic impedance intermediate the respective values of acoustic impedance pertaining to the object and to the remainder of said transducer.

22. The apparatus according to claim 14, wherein said ultrasound transducer is adapted for transmitting an ultrasound pulse wave at a first frequency and an ultrasound pulse wave at a second frequency into the body of the being and into the bone.

* * * * *